(12) United States Patent
Sahatjian et al.

(10) Patent No.: US 6,663,594 B2
(45) Date of Patent: Dec. 16, 2003

(54) IMMOBILIZING OBJECTS IN THE BODY

(75) Inventors: Ronald Sahatjian, Lexington, MA (US); Arthur Madenjian, Winchester, MA (US); Bill Little, Medway, MA (US)

(73) Assignee: SciMed Life Systems, Inc., Maple Grove, MN (US)

(*) Notice: Subject to any disclaimer, the term of this patent is extended or adjusted under 35 U.S.C. 154(b) by 0 days.

(21) Appl. No.: 10/403,768

(22) Filed: Mar. 31, 2003

(65) Prior Publication Data

US 2003/0195464 A1 Oct. 16, 2003

Related U.S. Application Data

(63) Continuation of application No. 10/083,835, filed on Feb. 28, 2000, now Pat. No. 6,544,227, which is a continuation-in-part of application No. 09/795,635, filed on Feb. 28, 2001, now Pat. No. 6,565,530.

(51) Int. Cl.[7] .................................................. A61F 7/12
(52) U.S. Cl. ...................... 604/113; 604/48; 604/93.01; 604/164.08; 606/22; 606/127; 606/128
(58) Field of Search ................................ 604/48, 93.01, 604/113, 164.08; 606/22, 27, 127, 128

(56) References Cited

U.S. PATENT DOCUMENTS

| 3,882,036 A | 5/1975 | Krezanoski et al. |
|---|---|---|
| 4,188,373 A | 2/1980 | Krezanoski |
| 4,478,822 A | 10/1984 | Haslam et al. |
| 4,542,542 A | 9/1985 | Wright |
| 4,696,297 A | 9/1987 | Pleines et al. |
| 4,997,435 A | 3/1991 | Demeter |
| 5,147,923 A | 9/1992 | Mueller |
| 5,330,768 A | 7/1994 | Park et al. |
| 5,348,746 A | 9/1994 | Dong et al. |
| 5,430,104 A | 7/1995 | Sio et al. |
| 5,444,097 A | 8/1995 | Tkacik |
| 5,484,610 A | 1/1996 | Bae |
| 5,542,928 A | 8/1996 | Evans et al. |
| 5,702,717 A | 12/1997 | Cha et al. |
| 5,861,174 A | 1/1999 | Stratton et al. |
| 5,906,623 A | 5/1999 | Peterson |
| 5,958,443 A | 9/1999 | Viegas et al. |
| 6,096,727 A | 8/2000 | Kuo et al. |
| 6,152,943 A | 11/2000 | Sawhney |
| 6,544,227 B2 * | 4/2003 | Sahatjian et al. ........... 604/113 |
| 6,565,530 B2 * | 5/2003 | Sahatjian et al. ........... 604/113 |

OTHER PUBLICATIONS

Brink et al., (Apr. 1983) "Glomerular Filtration in the Isolated Perfused Kidney. I. Sieving of Macromolecules," *Pflugers Arch*, vol. 397(1), pp. 42–47.

Abe et al., (Aug. 1990) "Evaluation of Pluronic F127 as a Base for Gradual Release of Anticancer Drug," *Gan To Kagaku Ryoho*, vol. 17, pp. 1546–1550.

Miyazaki et al., (Jun. 1995) "Percutaneous Absorption of Indomethacin from Pluronic F127 Gels in Rats," *Journal of Pharmaceutical Pharmacology*, vol. 47(6), pp. 455–457.

Batrakova et al., (Nov. 1996) "Anthracycline Antibiotics Non–Covalently Incorporated Into the Block Copolymer Micelles: In Vivo Evaluation of Anti–Cancer Activity," *British Journal of Cancer*, 74(10): 1545–1552.

(List continued on next page.)

Primary Examiner—Steven J. Ganey
(74) Attorney, Agent, or Firm—Testa, Hurwitz & Thibeault, LLP

(57) ABSTRACT

Stabilizing an object in the body of a patient involves the injection of a lower critical solution temperature (LCST) material or other flowable material into the body of the patient so that the material contacts the object. The LCST material or other flowable material then forms a gel in the body such that the object is contained at least partially within the gel and thereby stabilized by the gel such that the object can then be easily fragmented within the body and/or retrieved from the body.

24 Claims, 11 Drawing Sheets

OTHER PUBLICATIONS

R. Dagani, (Jun. 1997) "Intelligent Gels: Using Solvent–Swollen Polymer Networks that Respond to Stimuli, Scientists are Beginning to Develop a Soft, Wet, Organic Technology" *Chemical & Engineering News*.

Wirtanen et al., (Dec. 1998) "Performance Evaluation of Disinfectant Formulations Using Poloxamer–Hydrogel Biofilm–Constructs," *Journal of Applied Microbiology*, vol. 85(6), pp. 965–971.

Gilbert et al., (Dec. 1998) "The Use of Poloxamer Hydrogels for the Assessment of Biofilm Susceptibility Towards Biocide Treatments," *Journal of Applied Microbiology*, vol. 85(6), pp. 985–990.

Desai et al, (Oct. 1998) "Evaluation of Pluronic F127–Based Sustained–Release Ocular Delivery Systems for Pilocarpine Using the Albino Rabbit Eye Model," *Journal of Pharmaceutical Science*, vol. 87(10), pp. 1190–1195.

Scherlund et al., (Jan. 2000) "Thermosetting Microemulsions and Mixed Micellar Solutions as Drug Delivery Systems for Periodontal Anesthesia," *International Journal of Pharmacy*, vol. 194(1), pp. 103–116.

Moore et al., (Jul. 2000) "Experimental Investigation and Mathematical Modeling of Pluronic F127 Gel Dissolution: Drug Release in Stirred Systems," *Journal of Control Release*, vol. 67(2–3), pp. 191–202.

* cited by examiner

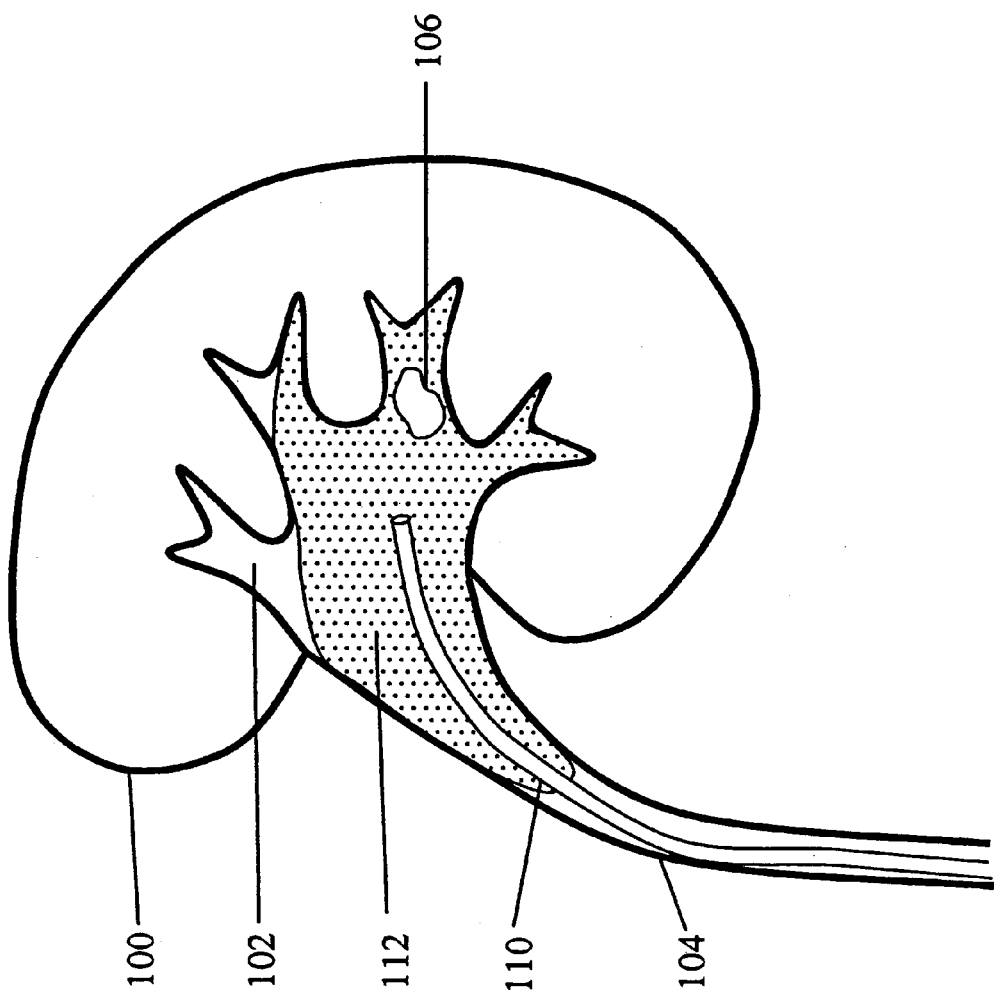

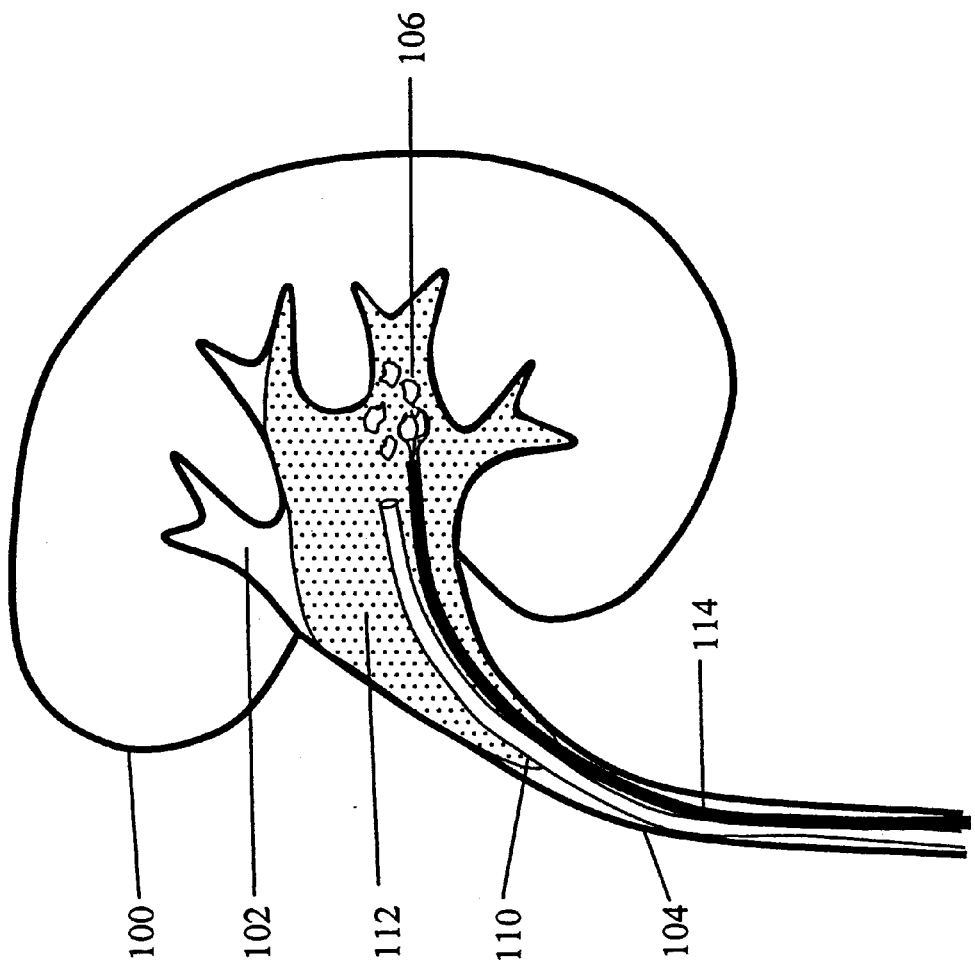

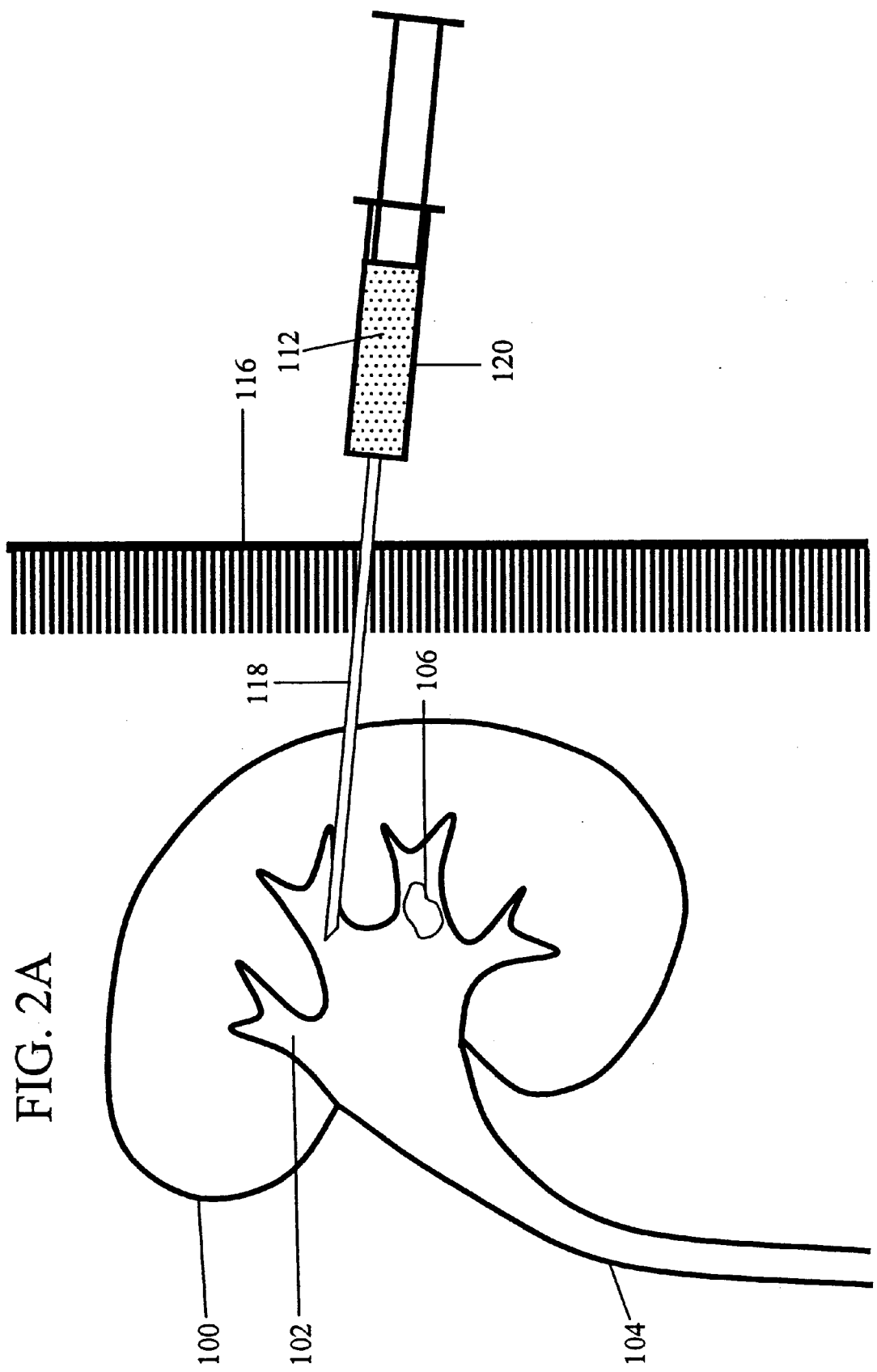

IMMOBILIZING OBJECTS IN THE BODY

CROSS-REFERENCE TO RELATED APPLICATIONS

This application is a continuation of U.S. patent application Ser. No. 10/083,835, filed Feb. 28, 2002, now U.S. Pat. No. 6,544,227 which is a continuation-in-part of U.S. patent application Ser. No. 09/795,635, filed on Feb. 28, 2001, now U.S. Pat. No. 6,565,530 the entire disclosure of which is incorporated by reference herein.

TECHNICAL FIELD

This invention generally relates to medical instruments and methods for retrieving material from within a body. More particularly, the invention relates to retrieval methods, devices, and compositions for stabilizing and removing stones such as urinary tract stones, gall stones, and other objects found in the body.

BACKGROUND INFORMATION

Medical retrieval devices generally are used to retrieve biological and foreign material, such as kidney stones and other calculi, from the body of a patient. Such medical retrieval devices may be used with an endoscope or a laparoscope. The use of such devices to capture foreign material like stones is made difficult by the freedom of movement of the stones within the body. A stone may dislodge from its resting place when contacted by a retrieval device. This may cause the stone to move into an area of the body that renders the stone inaccessible or undetectable, thus preventing the capture and removal of the stone.

Larger stones often need to be shattered because their size prohibits non-surgical removal from the body. Shattering a stone (by, for example, light, chemical, or physical energy) can disperse the resulting stone fragments from the original location of the stone. Stone fragments that are not removed from the body can form the nuclei for the formation of new stones. The dispersal of the fragments caused by the shattering process can cause fragments to move into inaccessible or unknown areas of the body, thus preventing or interfering with the capture and removal of the fragments.

SUMMARY OF THE INVENTION

It is an object of the invention to facilitate the capture and removal of objects located within the body. The invention generally includes the use of a material or materials that exist in liquid form and is transformed into a gel inside the body of a patient. In one aspect, the invention generally includes the use of a material that exists in liquid form at temperatures below about body temperature and as a gel at temperatures about at and above body temperature. The temperature at which the transition from liquid to gel occurs is referred to as the lower critical solution temperature (LCST), and it can be a small temperature range as opposed to a specific temperature. Materials appropriate for use according to the invention possess a LCST and are referred to as LCST materials.

The methods and systems of the present invention generally involve the injection of an LCST material into a cavity or space within the body. Once inside the body, the LCST material can contact and at least partially contain an object. In many cases, the LCST will entirely envelop and surround the object. As the temperature of the LCST material rises due to the internal temperature of the body, the LCST material will reach its LCST and thus transition into the gel phase. The specific transition point or range is determined by the specific LCST material utilized. An object in contact with the LCST material can be at least partially trapped and stabilized by the gel. The stabilization of the object allows for easier capture and retrieval of the object. Stabilization of the object also allows for easier use of a lithotripsy device for fragmenting the object because the gel holds the object in place. Furthermore, the gel prevents the free dispersal of fragments of the object after the object is broken apart by the lithotripsy device. Preventing the dispersal of the fragments allows for easier capture and retrieval of the object fragments.

The invention also relates to materials other than LCST materials that are in a flowable form outside of the patient's body and may be transformed into a gel form inside the patient's body. A material including crosslinkable polymers may be in a flowable form and upon contact with a crosslinking agent be transformed into gel form. The gel formed from a material including crosslinkable polymers functions similarly to the LCST material by contacting and stabilizing an object in the patient's body. The gel formed from the crosslinkable polymers may be dissolved by contact with a de-crosslinking agent. A de-crosslinking agent weakens or removes the bonds within the network of crosslinkable polymers that forms the gel. Once the gel is dissolved the material returns to a flowable form and may be more easily removed from the patient's body.

Other materials related to the invention include gelatin materials. Gelatin materials exist in liquid form at temperatures above about body temperature and as a gel at temperatures below about body temperature. The gelatin material is cooled after it is injected into the patient's body in order to transform the gelatin material into a gel form. Cooling of the gelatin material can be performed by contacting the gelatin material with a liquid that is at a temperature below about body temperature. Water or a buffer at a temperature below about body temperature may be injected concurrently with the injection of the gelatin material, for example.

The invention, in one aspect, includes a method of stabilizing an object in the body of a patient. The method includes injecting a lower critical solution temperature material in a flowable form into the body of the patient to contact the object. The method further includes allowing the lower critical solution temperature material to form a gel in the body due to a temperature inside the body. The object thus is contained at least partially within the gel and stabilized by the gel.

In one embodiment according to this aspect of the invention, the method involves the use of the lower critical solution temperature (LCST) material that remains in the flowable form below about the temperature inside the body of the patient. The LCST material can form the gel about at and above the temperature inside the body of the patient.

In other embodiments, the method can include retrieving the stabilized object from the gel and/or breaking the object into at least two fragments. At least some of the fragments remain at least partially within the gel and stabilized by the gel, and these fragments can then be retrieved from the gel.

In another aspect, the invention relates to a system for stabilizing an object in the body of a patient. The system includes a lower critical solution temperature material which remains in a flowable form below about a temperature inside the body of the patient and which forms a gel about at and above the temperature inside the body of the patient. The system also includes a catheter for transferring the lower critical solution temperature material into the body in the flowable form and a guide wire for introducing the catheter into the body and guiding it to about the location of the object. The system also includes a mechanism to force the lower critical solution temperature material in the flowable form through the catheter and into the body to contact the object. The lower critical solution temperature material gels inside the body due to the temperature inside the body and thereby contains at least a portion of the object within the gel to stabilize the object. One embodiment according to this aspect of the invention involves the use of the catheter to remove the lower critical solution temperature material from the body.

In still another aspect, the invention features a system for stabilizing an object in the body of a patient. The system includes a lower critical solution temperature material which remains in a flowable form below about a temperature inside the body of the patient and which forms a gel about at and above the temperature inside the body of the patient. The system also includes a percutaneous access device for transferring the lower critical solution temperature material into the body in the flowable form. The system further includes a mechanism to force the lower critical solution temperature material in the flowable form through the percutaneous access device and, into the body to contact the object. As before the lower critical solution temperature material gels once inside the body due to the temperature inside the body and thereby contains at least a portion of the object within the gel to stabilize the object.

In one embodiment according this aspect of the invention, the percutaneous access device comprises a needle. In some embodiments, the system further includes a catheter for removing the lower critical solution temperature material from the body. In some embodiments of this and the prior aspects of the invention, the mechanism used to force the lower critical solution temperature material into the body comprises a syringe.

The lower critical solution temperature material used in connection with all aspects of the invention can comprise a block copolymer with reverse thermal gelation properties. The block copolymer can further comprise a polyoxyethylene-polyoxypropylene block copolymer such as a biodegradable, biocompatible copolymer of polyethylene oxide and polypropylene oxide. Also, the lower critical solution temperature material can include a therapeutic agent such as an anti-angiogenic agent.

In another aspect, the invention relates to a method for stabilizing an object in a patient's body. The method includes injecting a first material, which includes a crosslinkable polymer in a flowable form, into the patient's body to contact an object. The method also includes contacting the first material with a second material. The second material includes a crosslinking agent, and the first material and second material, upon contact, form a gel in the patient's body. The method also includes stabilizing the object in the patient's body by enabling the gel to contact the object.

In an embodiment of the method, the first material includes one or more of an anionic crosslinkable polymer, a cationic crosslinkable polymer, or a non-ionically crosslinkable polymer. In other embodiments of the method, the first material includes one or more of polyacrylic acids, polymethacrylic acid, alginic acid, pectinic acids, sodium alginate, potasium alginate, carboxy methyl cellulose, hyaluronic acid, heparin, carboxymethyl starch, carboxymethyl dextran, heparin sulfate, chondroitin sulfate, polyethylene amine, polysaccharides, chitosan, carboxymethyl ichitosan, cationic starch or salts thereof.

In another embodiment of the method, the second material includes one or more of an anionic crosslinking ion, a cationic crosslinking ion, or a non-ionic crosslinking agent. In other embodiments of the method, the second material includes one or more of phosphate, citrate, borate, succinate, maleate, adipate, oxalate, calcium, magnesium, barium, strontium, boron, beryllium, aluminium, iron, copper, cobalt, lead, or silver ions. In still other embodiments of the method, the second material includes one or more of di-vinylsulfone, polycarboxylic acids, polycarboxylic anhydrides, polyamines, epihalohydrins, diepoxides, dialdehydes, diols, carboxylic acid halides, ketenes, polyfunctional aziridines, polyfunctional carbodiimides, polyisocyanate, glutaraldehyde, or polyfunctional crosslinkers including functional groups capable of reacting with organic acid groups.

In another embodiment, the method further includes the step of retrieving the object from the gel. In yet another embodiment, the method further includes the step of applying energy to the object causing it to break into at least two fragments. At least some of the fragments remain at least partially in contact with the gel and stabilized by the gel. In others embodiments of the method, the energy applied to the object is selected from the group consisting of mechanical, vibrational, light, chemical, and electromagnetic energy. In other embodiments of the method, the technique for breaking the object into at least two fragments is selected from the group consisting of extra-corporeal shock wave lithotripsy, intra-corporeal shock wave lithotripsy, or Holmium laser fragmentation.

In another embodiment, the method further includes the step of retrieving at least some of the fragments from the gel. In one embodiment, the step of retrieving some of the fragments from the gel includes using a retrieval device to retrieve such fragments.

In yet another embodiment, the method further includes contacting the gel with a third material that includes a de-crosslinking agent. In some embodiments, the third material includes one or more of sodium phosphate, sodium citrate, inorganic sulfates, ethylene diamine tetraacetic acid and ethylene dime tetraacetate, citrates, organic phosphates (e.g., cellulose phosphate), inorganic phosphates (e.g., pentasodium tripolyphosphate, mono- and di-basic potassium phosphate, sodium pyrophosphate), phosphoric acid, trisodium carboxymethyloxy succinate, nitrilotriacetic acid, maleic acid, oxalate, polyacrylic acid, sodium, potassium, calcium, or magnesium ions.

In another aspect, the invention relates a method of fragmenting an object in a patient's body. The method includes injecting a material in a flowable form into the patient's body to contact an object, allowing the material to form a gel in the patient's body, and stabilizing the object in the patient's body by enabling the gel to contact the object. The method also includes applying energy from outside of the patient's body that is directed towards the object. The energy directed towards the object breaks the object into at least two fragments. In one embodiment the energy is produced by extra-corporeal shock wave lithotripsy.

In one embodiment according to this aspect of the invention, the material includes one or more of a crosslinkable polymer, a gelatin material or a lower critical solution temperature material. In another embodiment, the material includes a polyoxyethylene-polyoxypropylene block copolymer.

In another embodiment, the method further includes retrieving the stabilized object from the gel. In yet another embodiment, the method further includes breaking the object into at least two fragments. At least some of the fragments remain in contact with the gel. In another embodiment, the method further includes retrieving the at least some of the fragments from the gel. In one embodiment, the method further includes contacting the lower critical solution temperature material with a degradation modulating material. In another embodiment, the degradation modulating material is selected from the group consisting of pluronic acid, polylactic acid, polyglycolic acid, and hyaluronic acid.

In another aspect, the invention relates to a system for stabilizing an object in a patient's body. The system includes a first material that includes a crosslinkable polymer in flowable form, and a second material that includes a crosslinking agent. The first material and second material, upon contact, form a gel in the patient's body. The system also includes a catheter for transferring the first material and second material into the patient's body in flowable form, such that the gel formed by the first material and second material contacts and thereby stabilizes the object. The system also includes a guide wire for introducing and guiding the catheter into the patient's body.

In yet another aspect, the invention relates to a system for stabilizing an object in a patient's body. The system includes a first material that includes a crosslinkable polymer in flowable form, and a second material that includes a crosslinking agent. The first material and second material, upon contact, form a gel in the patient's body. The system also includes a percutaneous access device for injecting the first material and second material into the patient's body in flowable form, such that the gel formed by the first material and second material contacts and thereby stabilizes the object.

In embodiments according to the aspects of the invention relating to a system, the first material includes one or more of an anionic crosslinkable polymer, a cationic crosslinkable polymer, or a non-ionically crosslinkable polymer. In other embodiments according to the aspects of the invention relating to a system to the first material includes one or more of polyacrylic acids, polymethacrylic acid, alginic acid, pectinic acids, sodium alginate, potassium alginate, carboxy methyl cellulose, hyaluronic acid, heparin, carboxymethyl starch, carboxymethyl dextran, heparin sulfate, chondroitin sulfate, polyethylene amine, polysaccharides, chitosan, carboxymethyl chitosan, cationic starch or salts thereof.

In yet other embodiments according to the aspects of the invention relating to a system, the second material includes one or more of an anionic crosslinking ion, a cationic crosslinking ion, or a non-ionic crosslinking agent. In other embodiments according to the aspects of the invention relating to a system, the second material includes one or more of phosphate, citrate, borate, succinate, maleate, adipate, oxalate, calcium, magnesium, barium, strontium, boron, beryllium, aluminium, iron, copper, cobalt, lead, or silver ions. In still other embodiments of the method, the second material includes one or more of di-vinylsulfone, polycarboxylic acids, polycarboxylic anhydrides, polyamines, epihalohydrins, diepoxides, dialdehydes, diols, carboxylic acid halides, ketenes, polyfunctional aziridines, polyfunctional carbodiimides, polyisocyanate, glutaraldehyde, or polyfunctional crosslinkers including functional groups capable of reacting with organic acid groups.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also the drawings are not necessarily to scale, emphasis instead generally being placed upon illustrating the principles of the invention.

FIG. 1b illustrates the insertion of a catheter into the kidney by passage over the guide wire of FIG. 1a.

FIG. 1c illustrates the removal of the guide wire from the lumen of the catheter of FIG. 1b and the injection of an LCST material into the kidney through the catheter.

FIG. 1e illustrates the capture of a kidney stone fragment by a medical retrieval device such as a basket.

FIG. 2a illustrates the percutaneous insertion of a needle, into a kidney containing a kidney stone, with a syringe containing an LCST material connected to the needle on the outside of the patient's body.

DESCRIPTION

Figure 1A:
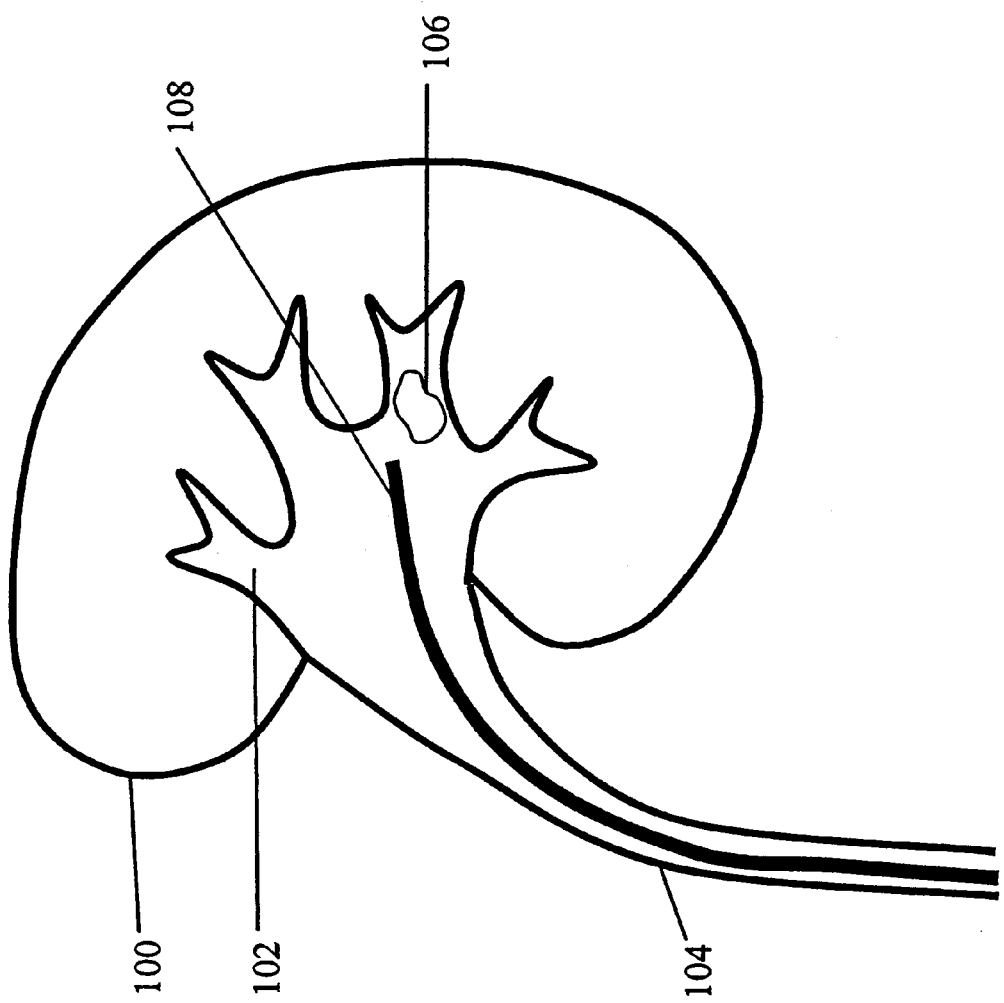
FIG. 1a illustrates the insertion of a distal end of a guide wire into a kidney containing a kidney stone.

The invention generally relates to systems and methods for stabilizing objects (such as kidney stones, gall stones, and other natural and foreign substances) found in the body of a patient (such as a human or other mammal) by the injection of a flowable material into the patient's body and the transformation of the material into a gel. The gel contacts and thereby stabilizes the object in the patient's body. The invention involves using materials that become a gel at or above about body temperature, materials that become a gel when contacted with a crosslinking agent, and gelatin materials that form a gel at temperatures below about body temperature.

The materials that are the subject of the invention, such as the LCST materials that become a gel at or about body temperature, can be injected into the patient's body in a liquid form. The injected material once reaching body temperature undergoes a transition from a liquid to a gel. Objects that are contacted by the material become trapped entirely or partially within the gel and thus stabilized in place in the body. Medical devices for breaking the object into fragments and/or retrieving (or otherwise eliminating) the object and any of its fragments from the body can accomplish the breaking and/or removal more easily because the gel causes the object to be fixed in place and does not allow the object to move freely about the cavity in which it is located in the body. Additionally, fragments of the object that result from breaking the object with a suitable medical device (such as a laser lithotriptor) generally remain trapped at least partially within the gel, in that the gel also traps the fragments and prevents the scattering of fragments within the body. Kidney stone fragments that remain in the body can form the nuclei for the growth of other kidney stones.

LCST materials possess a lower critical solution temperature, which is the temperature at which LCST materials transition from liquid to gel form. Suitable LCST materials include polyoxyethylene-polyoxypropylene (PEO-PPO) block copolymers. Two acceptable compounds are Pluronic acid F127 and F108, which are PEO-PPO block copolymers with molecular weights of 12,600 and 14,600, respectively. Each of these compounds is available from BASF of Mount Olive, N.J. Pluronic acid F108 at 20–28% concentration in phosphate buffered saline (PBS) is an example of a suitable LCST material. A more preferable preparation is 22.5% Pluronic acid F108 in PBS. A preparation of 22% Pluronic acid F108 in PBS has an LCST of 37° C. Pluronic acid F127 at 20–35% concentration in PBS is another example of a suitable LCST material. A preparation of 20% Pluronic acid F127 in PBS has an LCST of 37° C. Low concentrations of dye (such as crystal violet), hormones, therapeutic agents, fillers, and antibiotics can be added to the LCST material. For example, a cancer-treating agent such as endostatin can be carried by the LCST material and thus delivered inside the body via the LCST material. In general, other PEO-PPO block copolymers that are LCST materials and that are biocompatible, biodegradable, and exist as a gel at body temperature and a liquid at below body temperature can also be used according to the present invention. The molecular weight of a suitable material (such as a block copolymer) can be, for example, between 5,000 and 25,000, and more particularly between 7,000 and 15,000, and, for the two specific compounds identified above, 12,600 or 14,600.

Materials that include crosslinkable polymers and that become a gel when contacted with a crosslinking agent may be used in accordance with the invention. An embodiment of the invention relates to injecting a material including one or more crosslinkable polymers into the patient's body, contacting the crosslinkable polymers with a material including one or more crosslinking agents and enabling the gel to contact an object in the body. The material including crosslinkable polymer(s) may contact the material including crosslinking agent(s) before or after injection into the body. If the crosslinkable polymer(s) contact the crosslinking agent(s) before injection into the body, then mixture of crosslinkable polymer(s) and crosslinking agent(s) should be injected into the body prior to the crosslinking reaction occurring and the transformation of the materials into gel form. Contacting the gel formed with crosslinkable polymer (s) with a de-crosslinking agent dissolves the gel and facilitates its removal. Once the gel is dissolved, it flows down the ureter and into the bladder to be expelled from the body with the urine. The gel may also be removed by extraction of the material through a catheter or a percutaneous access device such as a needle.

Referring to FIG. 1a, distal end of a guide wire 108 is inserted into the urinary tract until reaching the kidney 100. The guide wire 108 can include a controllable tip for the purpose of directing the guide wire 108 along the urinary tract. The guide wire 108 could similarly be inserted into other tracts or passageways of the body. A stone 106 is present in the calyx 102 of the kidney 100. The stone 106 could also be located in other locations of the kidney 100 such as the renal pelvis or other locations in the urinary tract such as the ureter 104.

Figure 1B:
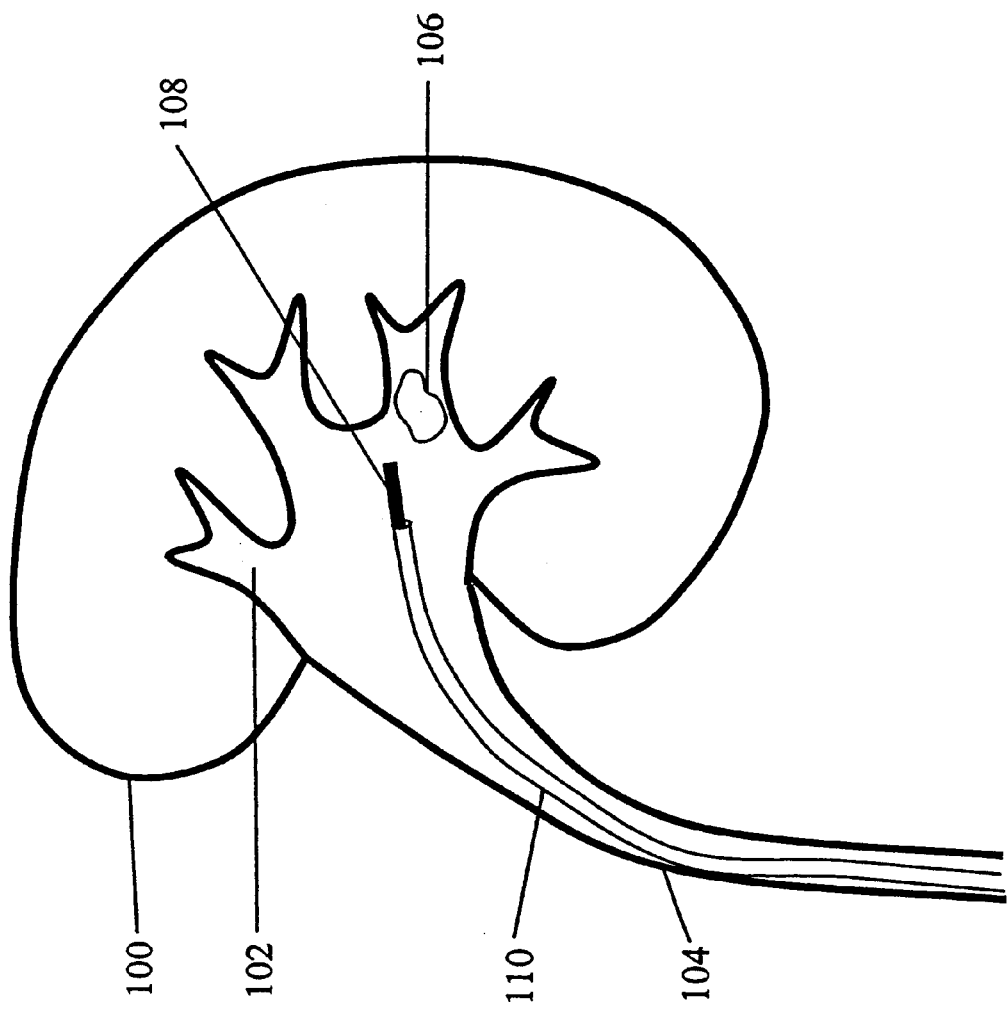

In FIG. 1b, the guide wire 108 serves as a guide for the insertion of the distal end of the catheter 110 into the kidney 100. The catheter 110 slides over the guide wire 108 with the guide wire 108 located in the lumen of the catheter 110. The catheter 110 may extend into the kidney so that the distal end of the catheter 110 is disposed near the kidney calyx 102 and the stone 106.

The guide wire 108 is then withdrawn from the lumen of the catheter 110 and is removed from the body, thus leaving the catheter 110 within the body. The lumen of the catheter 110, unobstructed by the guidewire 108, may transport material in flowable form from the outside of the patient's body into the patient's body and the calyx 102, for example. The LCST material 112, as an example of a material in a flowable form, starts external to the body and at a temperature below body temperature and thus in a liquid and flowable form. In some embodiments, the LCST material 112 could be cooled to a temperature below ambient air temperature prior to injection to delay the time required for the injected LCST material 112 to reach body temperature and form a gel, but such cooling generally is not required. A mechanism, such as an automated or human-operated syringe, can be used to force the LCST material 112 through the catheter 110 and into the kidney 100, as shown in FIG. 1c. The mechanism can be any suitable device that applies pressure to the LCST material 112 to force it in a liquid form through the catheter 110 and into the body to contact the object to be stabilized. The LCST material 112 then enters, as a liquid, areas of the kidney 100 including the calyx 102 and the renal pelvis. The LCST material 112 also generally flows into the ureter 104 and towards the urinary bladder, as depicted in FIG. 1c. As the temperature of the LCST material 112 inside the body rises toward body temperature, the LCST material 112 reaches its LCST and transitions into the gel phase. An object, like the stone 106, in contact with the LCST material 112 will be at least partially enveloped by the gel and thus stabilized by the gel. The stabilization of the stone 106 allows for easier capture and retrieval of the stone 106 because the stone 106 is held in place by the gel 112. Additionally, the transition from liquid to gel can cause the LCST material 112 to form a seal or plug in the ureter 104 near the renal pelvis that allows the LCST material 112 to accumulate in the kidney 100 instead of draining out of the ureter 104.

The introduction of other materials in flowable form into the patient's body is performed in substantially the same manner as the introduction of LCST material 112 into the patient's body. Materials used in accordance with the invention include crosslinkable polymers and crosslinking agents, which catalyze the transformation of the crosslinkable polymers from a flowable form into a gel form. The resulting gel is formed of an insoluble network of the crosslinkable polymers.

Crosslinkable polymers that may be suitable for use in the invention include both ionically crosslinkable and non-ionically crosslinkable polymers. To be used in conjunction with these crosslinkable polymers, crosslinking agents that may be employed include both ionic crosslinking agents and non-ionic crosslinking agents, respectfully. Ionically crosslinkable polymers include anionic crosslinkable polymers and cationic crosslinkable polymers that may be used in conjunction with anionic crosslinking agents and cationic crosslinking agents, respectively.

The anionic or cationic crosslinkable polymers may include, but are not limited to, at least one polymer or copolymer such as polyacrylic acids, polymethacrylic acid, alginic acid, pectinic acids, sodium alginate, potassium alginate, carboxy methyl cellulose, hyaluronic acid, heparin, carboxymethyl starch, carboxymethyl dextran, heparin sulfate, chondroitin sulfate, polyethylene amine, polysaccharides, chitosan, carboxymethyl chitosan, cationic starch or salts thereof. Illustrative examples of cationic crosslinking agents include polycations such as calcium, magnesium, barium, strontium, boron, beryllium, aluminium, iron, copper, cobalt, lead, and silver ions. Illustrative examples of anionic crosslinking agents include polyanions such as phosphate, citrate, borate, succinate, maleate, adipate and oxalate ions, and, more broadly, anions derived from polybasic organic or inorganic acids. The anionic or cationic crosslinking agents can either be a mono- or poly-charged ion.

The crosslinkable polymer also includes non-ionically crosslinkable polymers that are transformed from a flowable form to a gel form by contact with non-ionic crosslinking agents. Non-ionic crosslinking agents may also be used instead of or in addition to ionic crosslinking agents with ionically crosslinkable polymer. Thus, a higher crosslinking density and improved mechanical properties, i.e., improved stiffness, modulus, yield stress and strength, may be accomplished by additionally subjecting the ionically crosslinkable polymer to non-ionic crosslinking. For example, non-ionic crosslinking can be accomplished by treatment with a chemical crosslinking agent which reacts with groups present in the polymer such that covalent bonds are formed connecting different portions of the polymer or between polymer strands to form a network.

Suitable non-ionic crosslinking agents are polyfunctional compounds preferably having at least two functional groups reactive with one or more functional groups present in the polymer. The crosslinking agent can contain one or more of carboxyl, hydroxy, epoxy, halogen, amino functional groups or hydrogen unsaturated groups. Illustrative non-ionic crosslinking agents include di-vinylsulfone, polycarboxylic acids or anhydrides, polyamines, epihalohydrins, diepoxides, dialdehydes, diols, carboxylic acid halides, ketenes and like compounds. Illustrative crosslinkable polymers include those that possess organic acid functional groups that are covalently crosslinkable with polyfunctional crosslinking agents. The covalent bonds between the crosslinking agents and the hydrophilic polymers are susceptible to hydrolysis in the body, releasing water-soluble components.

One embodiment utilizes crosslinking agents that can form relatively weak covalent crosslinking bonds, so that these bonds can be de-crosslinked within the body after a desired length of time. For example, polymers comprising covalent bonds that are easily hydrolysable at temperature and pH conditions inside the body can serve this purpose. Such polyfunctional covalent crosslinking agents include polyfunctional aziridines, polyfunctional carbodiimides, polyisocyanate, glutaraldehyde or other polyfunctional crosslinkers wherein the functional groups are capable of reacting with the organic acid groups, or any activated forms thereof.

Alginate is an example of an ionically crosslinkable polymer. Alginate is a heterogeneous group of linear binary co-polymer of 1–4 linked β-D-mannuronic acid (M) and its C-5 epimer O-L-guluronic acid (G). The monomers are arranged in blockwise pattern along the polymer chain where mannuronic blocks (M blocks) and guluronic blocks (G blocks) are interspaced with sequences containing both M monomers and G monomers (mixed or MG blocks). The proportion and sequential arrangement of the uronic acids in alginate depend upon the species of algae and the kind of algal tissue from which the material is prepared. Commercial alginates are produced from sources including *Laminaria hyperborea, Macrocystis pyrifera, Laminaria digitata, Ascophyllum nodosum, Laminaria japonica, Eclonia maxima, Lesonia negrescens* and *Saragassum sp.*

Monovalent cation alginate salts, such as sodium or potassium alginate, are water soluble. Most divalent cations, such as calcium, strontium, or barium, interact with alginate to form water insoluble but water permeable gels. Because of the higher affinity of these divalent cations for guluronate compared with mannuronate blocks and because of steric considerations, cooperative binding of gelling divalent cations to guluronate within guluronate blocks provides the primary intermolecular crosslinking responsible for formation of stable alginate gels. Mannuronate and mixed blocks are not crosslinked due to their weaker affinity for the crosslinking divalent cation, but function as flexible interconnecting segments between interacted guluronate blocks.

Different divalent cations have different affinities for mannuronate and guluronate and thus are differentially susceptible to be displaced by exchange with other monovalent or divalent cations. Likewise, depending on the molecular weight, the number of residues per block and the overall ratio of guluronate to mixed or mannuronate blocks, different alginates have different susceptibilities to undergo ion exchange reactions.

The degree of crosslinking, both ionic and non-ionic, can be controlled mainly as a function of the concentrations of the crosslinking agents and crosslinkable polymers, such as alginate for example. The crosslinking agents and crosslinkable polymers may be in a solution of water or of another suitable solvent or mixture thereof. The solvent is not limited as long as it is suitable for the application. In solution, the concentrations of the crosslinking agent or crosslinkable polymers can range from about 0.0001 M to about 10 M and is to be determined according to the application.

Figure 1D:
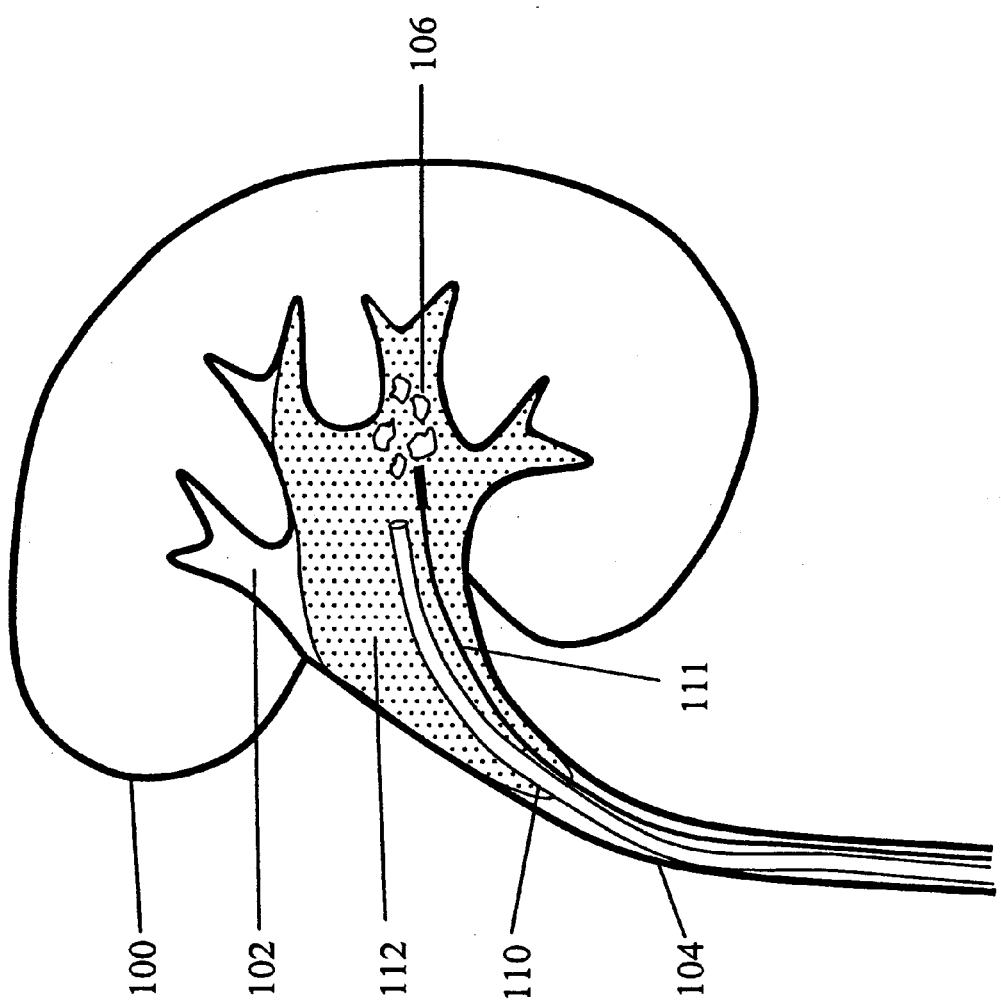
FIG. 1d is similar to FIG. 1c except that FIG. 1d shows the kidney stone after being fragmented by, for example, a medical lithotripsy device.

In FIG. 1d, the stone 106 is shown broken apart into fragments, and this fragmentation can be achieved generally by a medical device that delivers light, chemical, physical, or other type of energy to the stone 106. Intra-corporeal shock wave lithotripsy (ISWL) is a method of fragmenting a stone 106 with vibrational energy produced by a device internal to the patient's body. Energy transferred to stone may emanate from a device such as a fragmenting probe 111 placed inside the patient's body and near the targeted stone 106 in order to fragment the stone 106. The fragmenting probe 111 is inserted into the patient's body until reaching the general area in which the stone 106 resides. Once the stone 106 is targeted by the fragmenting probe 111, an energy is released from the fragmenting probe 111 and is at least partly absorbed by the stone 106 causing the stone 106 to fragment into at least two fragments. The energy released from the fragmenting probe 111 may be in the form of light from a Holmium laser, vibrational or shockwave energy, for example. The fragmenting probe 111 need not be inserted into the body via the ureter 104, but may also be inserted percutaneously. The fragmenting probe 111 may be removed from the patient's body once the fragmentation of the stone 106 is complete. Referring to FIGS. 2a–e, the fragmenting probe 111 is equally effective in the devices and methods in which the flowable material is injected into the patient's body percutaneously.

In FIG. 1e, a fragment or a whole stone 106 is captured by a medical retrieval device 114. The retrieval device 114 may be inserted into the kidney 100 via the urinary tract or through the catheter 110 or in some other manner. The retrieval device 114 can be a basket. The basket or other stone capturing device makes contact with the stone 106 and typically is manipulated by a human operator to ensnare the stone 106. Once the stone 106 is captured, the device 114 can be withdrawn from the body in order to remove the stone 106. The capture and removal of stones 106 or stone fragments can be repeated by reinserting the retrieval device 114. The LCST material 112, or other material that forms the gel, functions to stabilize the stones 106 or stone fragments during the possible multiple rounds of stone removal thus preventing dispersal of stones 106 or stone fragments throughout the kidney 100.

Figure 1F:
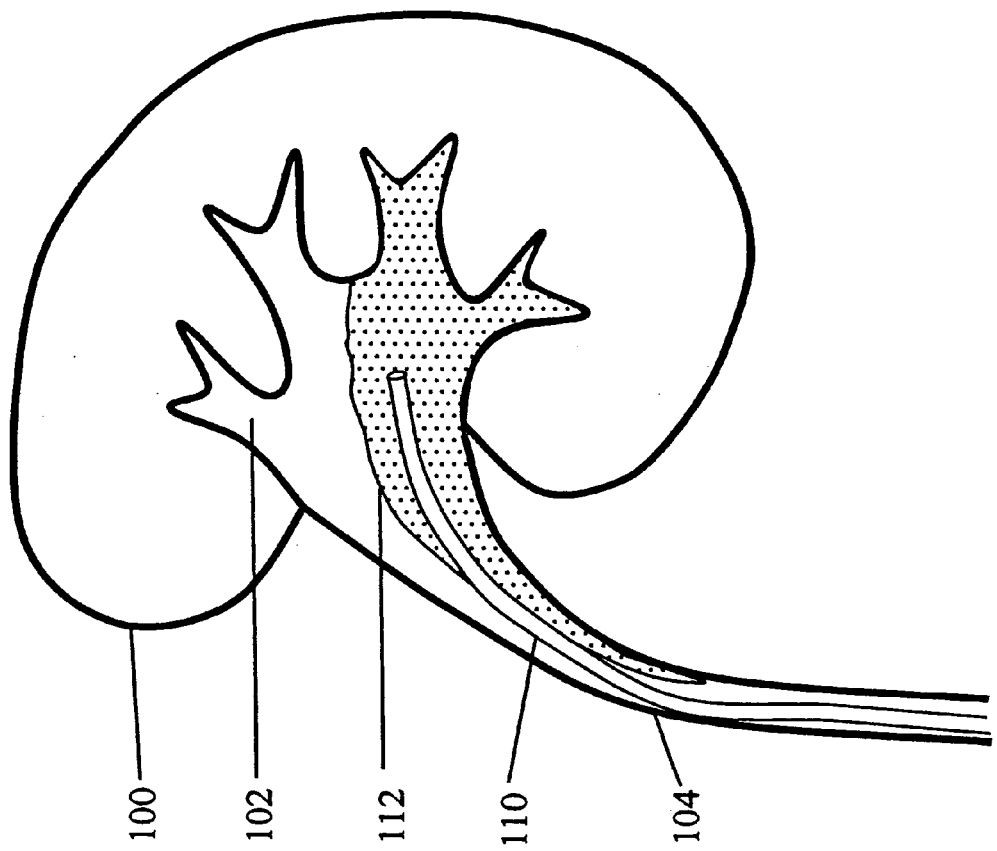
FIG. 1f shows the kidney after removal of the kidney stone fragments of FIGS. 1d and 1e, and after some of the LCST material has drained and/or been removed from the body.

In FIG. 1f, the retrieval device 114 has been withdrawn from the kidney 100. The LCST material 112 in gel form will break down and flush out of the body over time. To speed the removal of the gel from the body, a chilled fluid can be introduced into the body, but such a procedure generally is not required. If used, the fluid could be a physiologically acceptable liquid such as water, saline, contrast media, or other fluid having temperature below the LCST of the LCST material 112. The preferred temperature of the chilled fluid is, for example, −10° C. to 20° C., and more preferably 0° C. to 10° C. The fluid may be chilled by packing the fluid in ice, refrigerating the fluid or other means. The fluid could be introduced into the gel 112 through the catheter 110. The catheter 110 can be used to remove (by, for example, suction) at least some of the LCST material 112, whether or not the gel is cooled to return it to its flowable liquid form. In one preferred embodiment, a cooling fluid is not used in either the delivery or removal of the LCST material, and instead the gel is eliminated naturally from the body over time. The catheter 110 could be an independent tubular structure as shown. Alternatively, catheter 110 could be incorporated as part of a medical device that is inserted into the kidney 100 such as a tool that breaks apart the stone 106 or collects stone fragments.

The material including crosslinkable polymers that forms a gel may be dissolved to assist in the removal of the gel from the patient's body. The gel formed from crosslinkable polymers may include or be exposed to a de-crosslinking agent which functions by displacing a crosslinking agent within the network of crosslinkable polymers that forms the gel. Suitable de-crosslinking agents include sodium phosphate, sodium citrate, inorganic sulfates, ethylene diamine tetraacetic acid and ethylene dime tetraacetate, citrates, organic phosphates (e.g., cellulose phosphate), inorganic phosphates (e.g., pentasodium tripolyphosphate, mono- and di-basic potassium phosphate, sodium pyrophosphate), phosphoric acid, trisodium carboxymethyloxy succinate, nitrilotriacetic acid, maleic acid, oxalate, polyacrylic acid, sodium, potassium, calcium, or magnesium ions.

The de-crosslinking agent may be added to the gel using an appropriate technique. Methods for triggered de-crosslinking include administering or triggering release of the de-crosslinking agent through the diet, administering the de-crosslinking agent directly into the gel in an aqueous solution, encapsulating the de-crosslinking agent in the gel, and enema. Once the de-crosslinking agent comes in contact with the gel formed from crosslinkable polymers, the bonds between the crosslinkable polymers that create the network that forms the gel will weaken or break causing the crosslinkable polymers to transform into a flowable form. Once in a flowable form the crosslinkable polymers can flow out of the patient's body via the ureter 104 and be extracted by a catheter 110 or a percutaneous access device such as a needle 118.

Figure 2B:
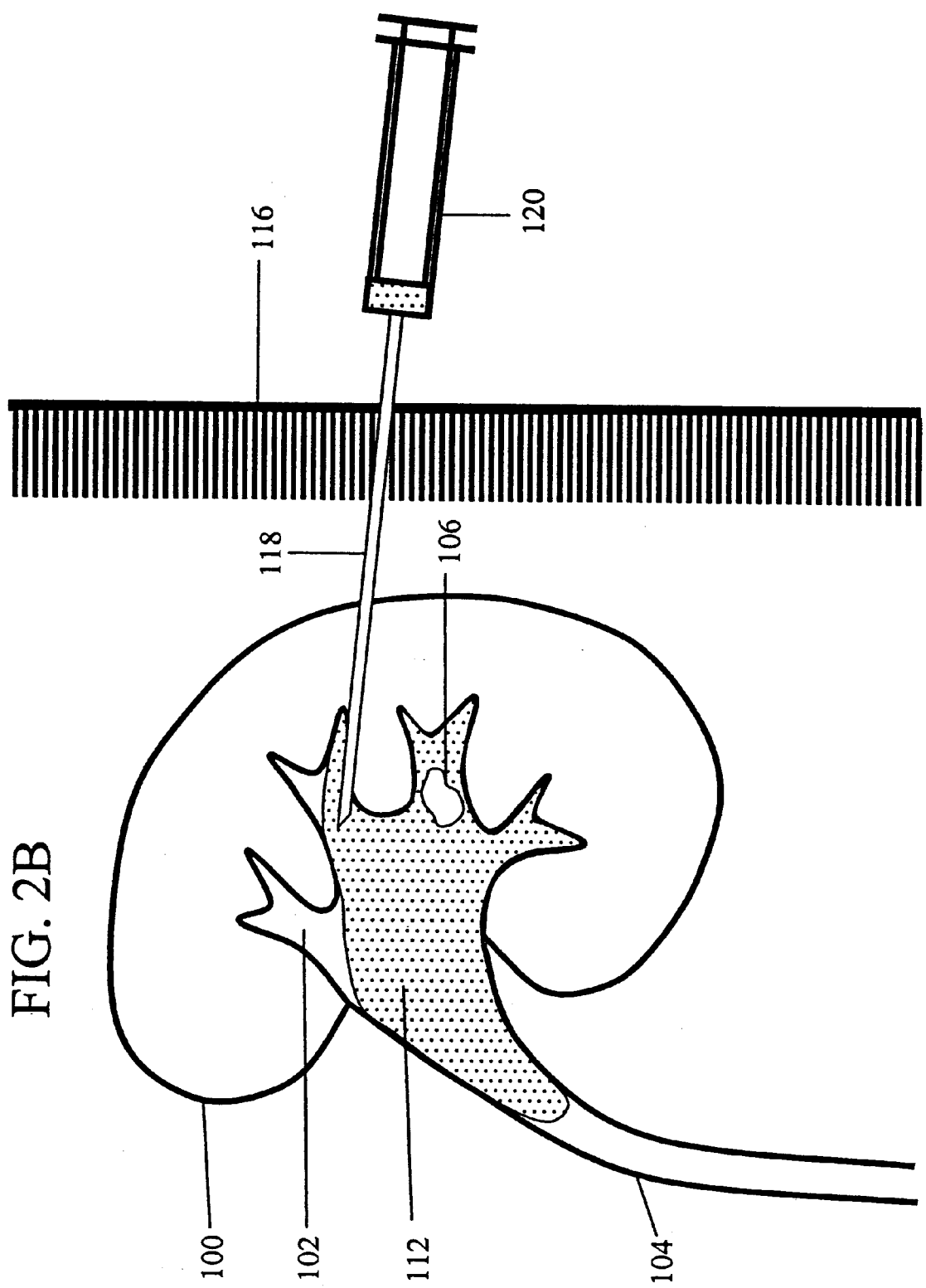
FIG. 2b illustrates the injection of the LCST material from the syringe, through the needle, and into the kidney.

FIGS. 2a–e generally depict methods and systems of the invention that are similar to the methods and systems depicted in FIGS. 1a–f. A primary difference between the two sets of drawings is the way the LCST material 112 or other flowable materials that form a gel in the patient's body is introduced into the patient's body. Referring to FIG. 2a, a needle 118 is inserted percutaneously through the skin 116 and into the body of the patient through the wall of the kidney 100 until reaching the calyx 102. A stone 106 is present in the calyx 102 of the kidney 100. The stone 106 could also be located in other locations of the kidney 100 such as the renal pelvis or other locations in the urinary tract such as the ureter 104.

LCST material 112, similar to the methods and devices depicted in FIGS. 1a–e, is an example of the many types of materials that exist in a flowable form outside the patient's body and are transformed into gel form while in the patient's body. Such materials, that include the crosslinkable polymers and gelatin materials previously described in FIGS. 1a–e, are equally applicable to the methods and devices described in FIGS. 2a–e.

The LCST material 112 starts external to the body, at a temperature below body temperature and in a liquid and flowable form. In some embodiments, the LCST material 112 could be cooled to a temperature below ambient air temperature prior to injection to delay the time required for the injected LCST material 112 to reach body temperature and form a gel, but such cooling generally is not required. A mechanism, such as an automated or human-operated syringe, can be used to force the LCST material 112, or other flowable materials, through the needle 118 and into the kidney 100, as shown in FIG. 2b. The mechanism can be any suitable device that applies pressure to the LCST material 112 to force it in a liquid form through the needle 118 and into the body to contact the object to be stabilized. The LCST material 112 then enters, as a liquid, areas of the kidney 100 including the calyx 102 and the renal pelvis. The LCST material 112 also generally flows into the ureter 104 and towards the urinary bladder, as depicted in FIG. 2b. As the temperature of the LCST material 112 inside the body rises toward body temperature, the LCST material 112 reaches its LCST and transitions into the gel phase. An object, like the stone 106, in contact with the LCST material 112 will be at least partially enveloped by the gel and thus stabilized by the gel. The stabilization of the stone 106 allows for easier capture and retrieval of the stone 106 because the stone 106 is held in place by the gel 112. Additionally, the transition from liquid to gel can cause the LCST material 112 to form a seal or plug in the ureter 104 near the renal pelvis that allows the LCST material 112 to accumulate in the kidney 100 instead of draining out of the ureter 104.

Figure 2C:
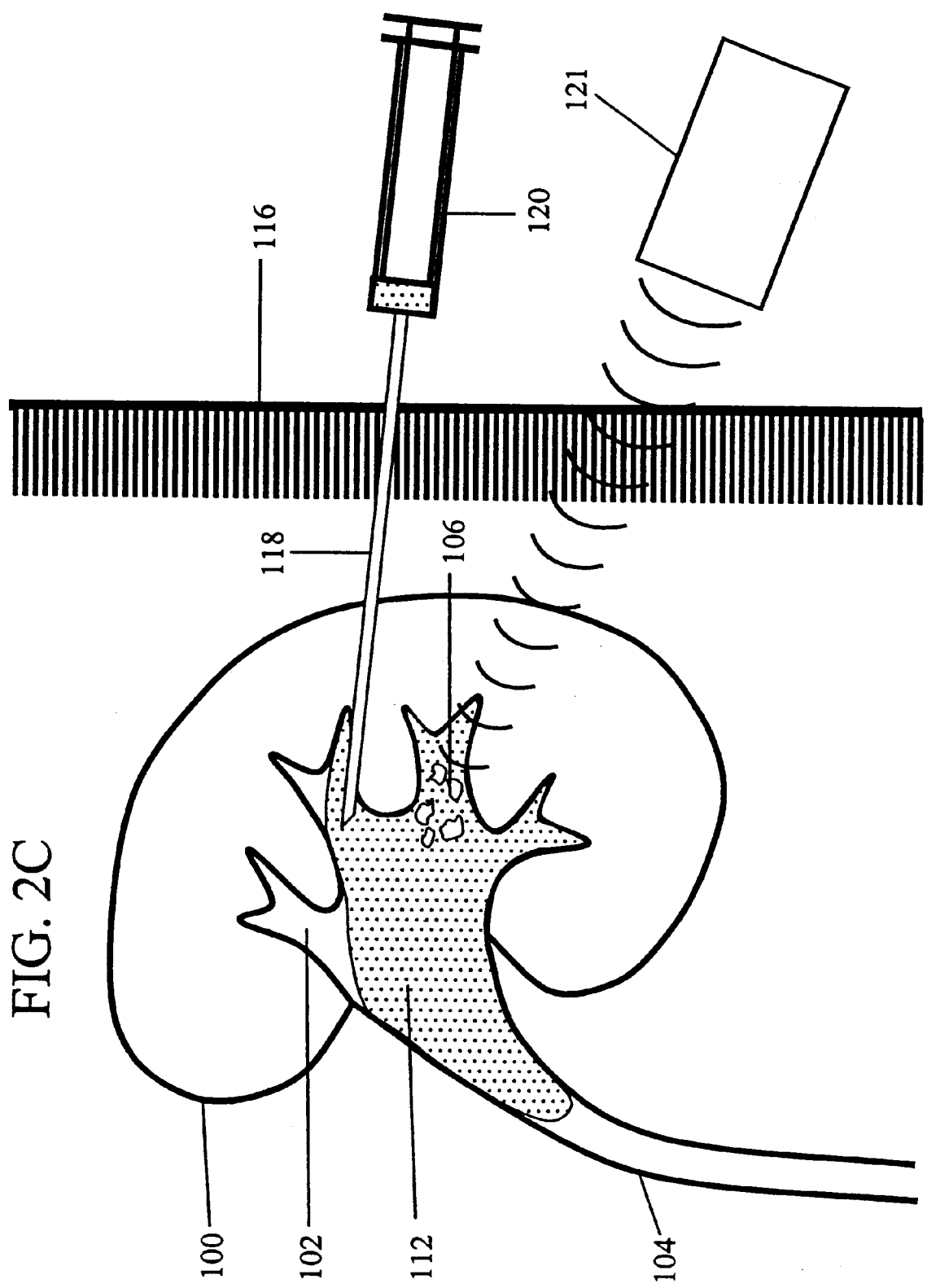
FIG. 2c shows the kidney stone after being fragmented by, for example, a medical lithotripsy device.

In FIG. 2c, the stone 106 is shown broken apart into fragments, and this fragmentation can be achieved by a device that delivers light, chemical, physical, or other type of energy to the stone 106. Following the breaking apart of the stone 106, the fragments of the stone 106 do not disperse throughout areas of the kidney. The gel formed from the LCST material 112 generally does not allow the fragments to escape, and the gel, retains and stabilizes the fragments. The gel generally absorbs at least some of the energy imparted to the stone 106 to cause it to break apart, and thus the gel prevents the fragments of stone 106 and the stone 106 itself from dispersing throughout the kidney 100.

Additionally, energy transferred to the stone 106 may emanate from outside the patient's body, from a lithotripter 121 for example, and travel through the patient's body until reaching the stone 106 targeted for fragmentation in a process called extracorporeal shock wave lithotripsy (ESWL). ESWL is a method of stone fragmentation commonly used to treat kidney stone disease. Various lithotripters 121 and methods exist for generating high-intensity, focused shock waves for the fragmentation of objects, such as kidney stones 106, inside a human being and confined in a body liquid. A lithotripter 121 generating a spark gap discharge in water has been used to generate a shock wave within an ellipsoidal reflector, which couples and focuses the shock wave to fragment kidney stones 106 inside the patient's body. Lithotripters 121 also exist that use a coil and a mating radiator, in the form of a spherical segment, to produce magnetically induced self-converging shock waves that can be directed at a stone 106 within the patient's body. A lithotripter 121 also exists that features piezoelectric elements arranged in mosaic form on a spheroidal cap have also been used to produce focused high-intensity shock waves at the geometric center of the cap, where the stone 106 must be placed.

Following the fragmentation of the stone 106 by ESWL, for example, the fragments of the stone 106 do not disperse throughout areas of the kidney. The gel formed from the LCST material 112 generally does not allow the fragments to escape, and the gel retains and stabilizes the fragments. The gel generally absorbs at least some of the energy imparted to the stone 106 to cause it to break apart, and thus the gel prevents the fragments of stone 106 and the stone 106 itself from dispersing throughout the kidney 100. ESWL is equally applicable to the system and methods described in FIGS. 1*a–e*.

Figure 2D:
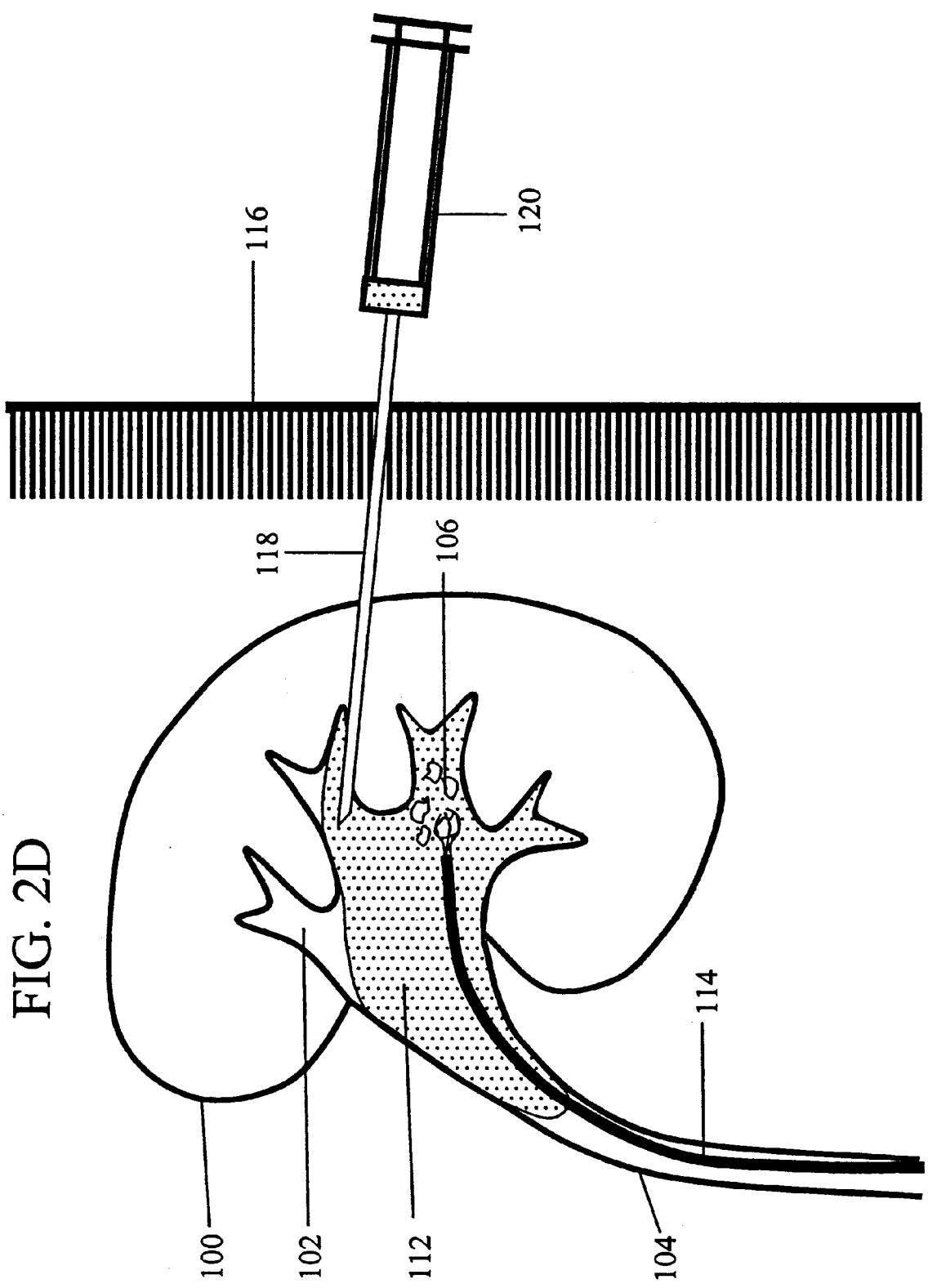
FIG. 2d illustrates the capture of a kidney stone fragment by a medical retrieval device such as a basket.

In FIG. 2*d,* a fragment or a whole stone 106 is captured by a medical retrieval device 114. The retrieval device 114 may be inserted into the kidney 100 via the urinary tract or through the catheter 110 or in some other manner. The retrieval device 114 may include a basket. The basket or other stone capturing device makes contact with the stone 106 and typically is manipulated by a human operator to ensnare the stone 106. Once the stone 106 is captured, the device 114 can be withdrawn from the body in order to remove the stone 106. The capture and removal of stones 106 or stone fragments can be repeated by reinserting the retrieval device 114. The LCST material 112 that forms the gel functions to stabilize the stones 106 or stone fragments during the possible multiple rounds of stone removal thus preventing dispersal of stones 106 or stone fragments throughout the kidney 100. Additionally, the needle 118 may be used to extract both the LCST material 112 and the stone fragments 106.

Figure 2E:
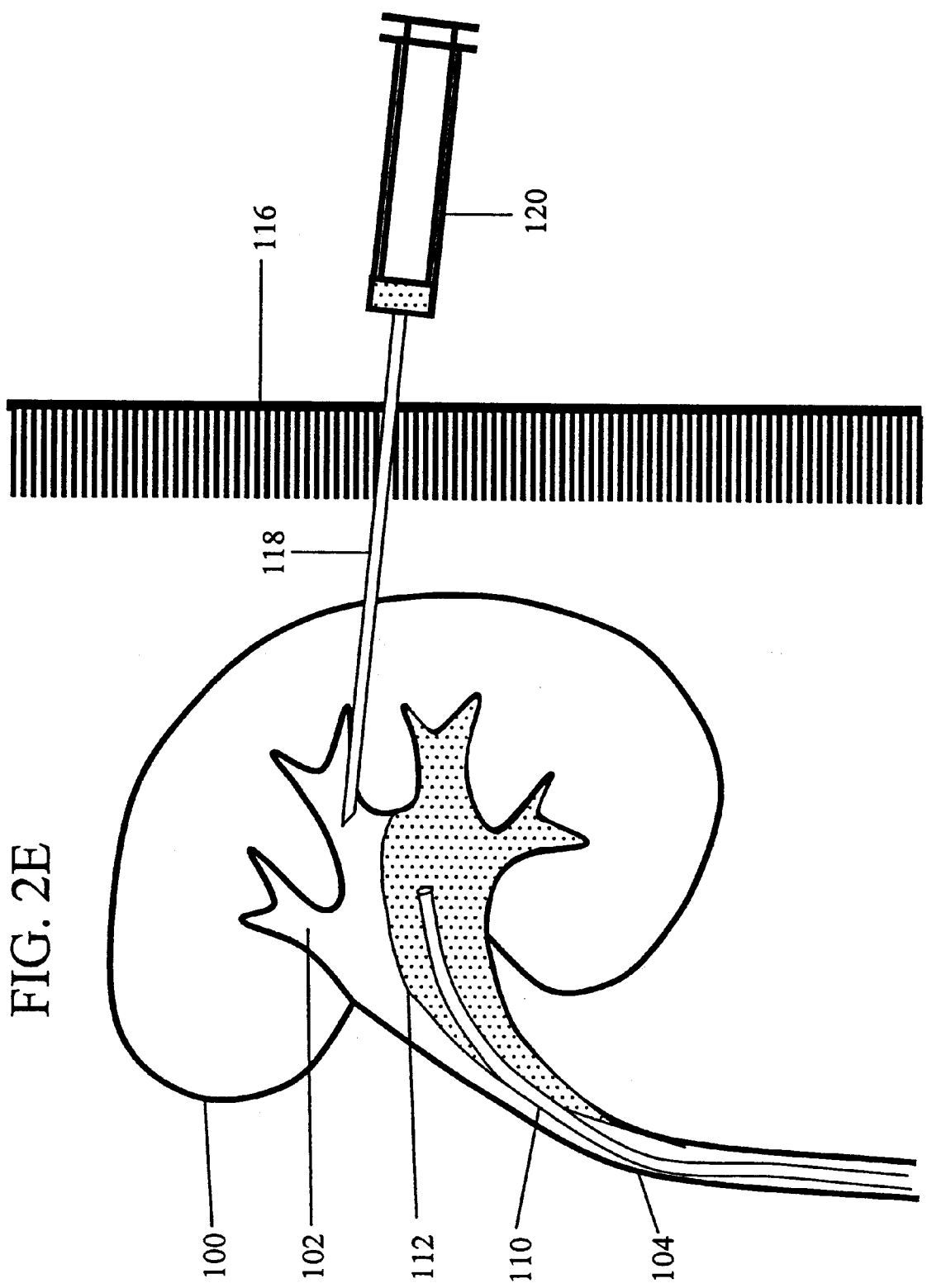
FIG. 2e shows the kidney after removal of the kidney stone fragments and after some of the LCST material has drained and/or been removed from the body.

In FIG. 2*e,* the retrieval device 114 has been withdrawn from the kidney 100. The LCST material 112 in gel form will break down and flush out of the body over time. To speed the removal of the gel from the body, a chilled fluid can be introduced into the body, but such a procedure generally is not required. If used, the fluid could be a physiologically acceptable liquid such as water, saline, contrast media, or other fluid having temperature below the LCST of the LCST material 112. The preferred temperature of the chilled fluid is, for example, −10° C. to 20° C., and more preferably 0° C. to 10° C. The fluid may be chilled by packing the fluid in ice, refrigerating the fluid or other means. The fluid could be introduced into the gel 112 through the needle 118. Additionally, a catheter 110 can be used to remove (by, for example, suction) at least some of the LCST material 112, whether or not the gel is cooled to return it to its flowable liquid form. In one preferred embodiment, a cooling fluid is not used in either the delivery or removal of the LCST material, and instead the gel is eliminated naturally from the body over time. The needle 118 could be an independent tubular structure as shown. Alternatively, needle 118 could be incorporated as part of a medical device that is inserted into the kidney 100 such as a tool that breaks apart the stone 106 or collects stone fragments.

The LCST material 112 used to stabilize an object in the body can also function as a carrier for chemical compounds, drugs, hormones, dyes or other additives to enhance the effectiveness, safety or functionality of the gel. The LCST gel mixture may include a dye to aid in determining the presence of the LCST material 112. The LCST gel mixture can also include antibiotics and anti-microbial agents, and such a mixture may assist in protecting the kidney against infection as a result of an invasive surgical procedure. The LCST gel mixture can also include one or more anti-inflammatory agents, which may assist in preventing inflammation in the kidney as a result of an invasive surgical procedure. Anesthetic agents may also be included in the LCST mixture in order to assist in numbing the pain associated with the surgical procedure. The LCST material 112 can also contain therapeutic agents. The therapeutic agents may include anti-angiogenic agents such as endostatin, angiostatin and thrombospondin. A LCST mixture containing anti-angiogenic agents could be used to treat cancerous tumors.

The catheter 110 can be used to dispense one or more fluids other than or in addition to the LCST material. The catheter 110 also can be a dilatation catheter with the ability also to dispense one or more fluids other than or in addition to the LCST material. In one embodiment, the catheter 110 is 4–8 french in size, and more preferably 5–6 french.

The syringe or other mechanism used to inject the LCST material 112 in liquid form into the body can be, for example, a 5–100 cc syringe such as a syringe with volume of 5–30 cc or with a volume of 5–10 cc. Pressure applied to the syringe can be applied by hand or by an automated syringe pusher.

While the invention has been described above mainly in connection with the stabilization and then removal and/or fragmentation of a kidney stone, the invention has applicability to object stabilization, removal, and fragmentation generally. A variety of stones and other objects, other than kidney stones, can be acted on in accordance with the invention, such as gall stones and biliary stones. Also, a variety of locations within the body of a patient can be accessed and treated according to the invention, such as other parts of the male or female urinary system, the gastrointestinal system, the biliary system, and the pancreatic duct.

It will be apparent to those skilled in the art that various modifications and variations can be made to the above-described structure and methodology without departing from the scope or spirit of the invention.

What is claimed is:

1. A method for stabilizing an object in a patient's body comprising:
   contacting a first material comprising a crosslinking polymer in a flowable form with a second material comprising a crosslinking agent to form a mixture;
   injecting the mixture into the body to contact the object before transformation of the mixture into gel form; and
   stabilizing the object by forming a gel that contacts the object in the patient's body.

2. The method of claim 1 wherein the first material comprises one or more of an anionic crosslinkable polymer, a cationic crosslinkable polymer, or a non-ionically crosslinkable polymer.

3. The method of claim 1 wherein the first material comprises one or more of polyacrylic acids, polymethacrylic acid, alginic acid, pectinic acids, sodium alginate, potassium alginate, carboxy methyl cellulose, hyaluronic acid, heparin, carboxymethyl starch, carboxymethyl dextran, heparin sulfate, chondroitin sulfate, polyethylene amine, polysaccharides, chitosan, carboxymethyl chitosan, cationic starch or salts thereof.

4. The method of claim 1 wherein the second material comprises one or more of an anionic crosslinking ion, a cationic crosslinking ion, or a non-ionic crosslinking agent.

5. The method of claim 1 wherein the second material comprises one or more of phosphate, citrate, borate, succinate, maleate, adipate, oxalate, calcium, magnesium, barium, strontium, boron, beryllium, aluminium, iron, copper, cobalt, lead, or silver ions.

6. The method of claim 1 wherein the second material comprises one or more of di-vinylsulfone, polycarboxylic acids, polycarboxylic anhydrides, polyamines, epihalohydrins, diepoxides, dialdehydes, diols, carboxylic acid halides, ketenes, polyfunctional aziridines, polyfunctional carbodiimides, polyisocyanate, glutaraldehyde, or polyfunctional crosslinkers including functional groups capable of reacting with organic acid groups.

7. The method of claim 1 further comprising the step of retrieving the object from the gel.

8. The method of claim 1 further comprising the step of applying energy to the object causing it to break into at least two fragments, at least some of the fragments remaining at least partially in contact with the gel and stabilized by the gel.

9. The method of claim 8 wherein the energy is selected from the group consisting of mechanical, vibrational, light, chemical, and electromagnetic energy.

10. The method of claim 8 wherein the object is broken into at least two fragments by technique selected from the group consisting of extra-corporeal shock wave lithotripsy, intra-corporeal shock wave lithotripsy, or Holmium laser fragmentation.

11. The method of claim 8 further comprising the step of retrieving at least some of the fragments from the gel.

12. The method of claim 11 wherein the step of retrieving at least some of the fragments from the gel includes using a retrieval device to retrieve such fragments.

13. The method of claim 1 further comprising contacting the gel with a third material comprising a de-crosslinking agent.

14. The method of claim 13 wherein the third material comprises one or more of sodium phosphate, sodium citrate, inorganic sulfates, ethylene diamine tetraacetic acid and ethylene dime tetraacetate, citrates, organic phosphates (e.g., cellulose phosphate), inorganic phosphates (e.g., pentasodium tripolyphosphate, mono- and di-basic potassium phosphate, sodium pyrophosphate), phosphoric acid, trisodium carboxymethyloxy succinate, nitrilotriacetic acid, maleic acid, oxalate, polyacrylic acid, sodium, potassium, calcium, or magnesium ions.

15. A method of fragmenting an object in a patient's body comprising:
    contacting a first material in flowable form with a second material to form a mixture;
    injecting the mixture into the body before transformation of the mixture into gel form;
    stabilizing the object by forming a gel that contacts the object in the patient's body; and
    directing energy towards the object, the energy breaking the object into at least two fragments.

16. The method of claim 15 wherein the energy is produced by extra-corporeal shock wave lithotripsy.

17. The method of claim 15 wherein the first material comprises one or more of a crosslinkable polymer, a gelatin material or a lower critical solution temperature material.

18. The method of claim 17 wherein the first material comprises the lower critical solution temperature material, further comprising contacting the lower critical solution temperature material with a degradation modulating material.

19. The method of claim 18 wherein the degradation modulating material is selected from the group consisting of pluronic acid, polylactic acid, polyglycolic acid, and hyaluronic acid.

20. The method of claim 15 wherein the first material comprises a polyoxyethylene-polyoxypropylene block copolymer.

21. The method of claim 15 further comprising the step of retrieving the stabilized object from the gel.

22. The method of claim 15 further comprising the step of breaking the object into at least two fragments, at least some of the fragments remaining in contact with the gel.

23. The method of claim 22 further comprising the step of retrieving the at least some of the fragments from the gel.

24. A method for stabilizing an object in a patient's body comprising:
    contacting a first material comprising a crosslinkable polymer in a flowable form with a second material comprising a crosslinking agent to form a mixture;
    injecting the mixture into the body to contact the object before transformation of the mixture into gel form;
    stabilizing the object by forming a gel that contacts the object in the patient's body; and
    administering a third material comprising a de-crosslinking agent into the patient's body to dissolve and facilitate removal of the gel.

* * * * *